United States Patent [19]

Ganz

[11] 4,329,312
[45] May 11, 1982

[54] METHOD OF MAKING GLOVES

[75] Inventor: Rudolph V. Ganz, Canton, Ohio

[73] Assignee: Affiliated Hospital Products, Inc., St. Louis, Mo.

[21] Appl. No.: 621,610

[22] Filed: Oct. 10, 1975

Related U.S. Application Data

[63] Continuation of Ser. No. 447,581, Mar. 4, 1974, abandoned, Ser. No. 292,492, Sep. 27, 1972, abandoned, Ser. No. 154,641, Jun. 18, 1971, abandoned, and Ser. No. 876,812, Nov. 14, 1969, abandoned.

[51] Int. Cl.$^3$ .............................................. B29H 3/04
[52] U.S. Cl. ................................... 264/306; 264/309; 2/168
[58] Field of Search ............... 264/306, 309, DIG. 72; 2/168

[56] References Cited

U.S. PATENT DOCUMENTS

| | | | |
|---|---|---|---|
| 1,997,874 | 4/1935 | Power | 264/309 |
| 2,120,406 | 6/1938 | Hansen | 264/306 |
| 2,165,099 | 7/1939 | Hansen | 264/309 |
| 3,689,613 | 9/1972 | Talalay | 264/306 |

Primary Examiner—Donald E. Czaja
Assistant Examiner—James R. Hall
Attorney, Agent, or Firm—Reginald F. Pippin, Jr.

[57] ABSTRACT

Method of forming a rubber latex glove having a textured interior surface and a textured exterior surface, one of the textured surfaces being transfer textured and the other textured surface being formed by impact spray on a molded rubber latex film with liquid rubber latex droplets while the film is in uncured condition.

24 Claims, 5 Drawing Figures

METHOD OF MAKING GLOVES

This application is a continuation of applications Ser. No. 447,581, filed Mar. 4, 1974, now abandoned, Ser. No. 292,492, filed Sept. 27, 1972, now abandoned Ser. No. 154,641, filed June 18, 1971, now abandoned and Ser. No. 876,812, filed Nov. 14, 1969, now abandoned.

This invention relates to a method of forming a rubber latex glove having a special spray textured surface.

It is desirable in surgical gloves to provide roughened or textured inner and outer surfaces. However, although various attempts have been made to provide double roughened or textured surfaced gloves, none have to my knowledge been fully satisfactory, due to various factors. It is accordingly a feature of this invention to provide an improved rubber latex glove having a textured exterior palm, fingers and thumb gripping surface and a textured interior surface of overall unique construction, and of particularly unique construction in the exterior textured surface thereof.

Briefly, according to the present invention a seamless integral rubber latex glove is formed by dipping a textured surfaced form sequentially into coagulant and rubber latex baths and impacting the uncured resultant film on the form with fine droplets of uncured liquid rubber latex in the form of a spray to thereby form impact craters and a build-up of walled craters and random plateau accumulations on the film surface. The spray is directed at the palm side of the film on the glove form, and is formed by multiple spray nozzles whose spray paths intersect in order to provide desired gripping surface coverage by the spray droplets. The resulting glove has the following features:

1. The improved textured exterior gripping surface provides quite adequate grip on surgical instruments and body tissues that tend to become slippery in the normal body fluids.
2. The inside textured surface reduces likelihood of slippage of the surgeon's hand inside the glove during a surgical procedure, normally caused by perspiration, as the textured inner surface apparently enables the perspiration to flow away from any pressured surface without "skating" of the glove over the hand surface.
3. The textured inner surface provides a stippled effect which appears to reduce the skin-to-glove coefficient of friction, as the gloves require less pull and effort to don.
4. The stipple textured inner surface reduces skin contact area and thereby reduces the likelihood of dermatitis.
5. Reduction in exterior gripping surface tackiness, normally associated with introduction of ordinary rubber latex film into body fluids, such as blood, mucous, etc.
6. The inner and outer finely textured homogeneous integral film rubber latex construction of the glove provides a highly pliable, soft and touch-sensitive glove, whereby body tissue can be contacted and examined and instruments can be handled with a high degree of sensitivity while wearing the glove.

Still other objects, features and attendant advantages will become apparent to one skilled in the art from a reading of the following detailed description of a preferred physical embodiment constructed in accordance with the invention, taken in conjunction with the accompanying drawings wherein.

Figure 1:
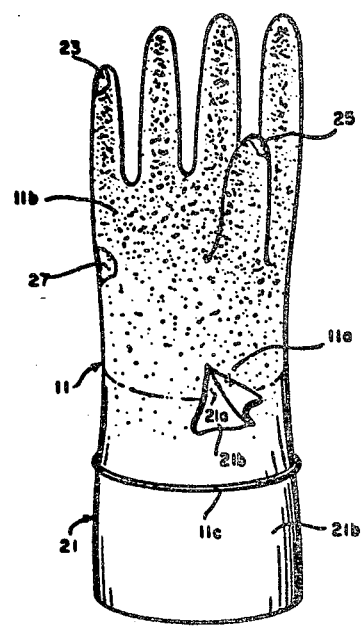
FIG. 1 is a schematic view of a glove according to the invention, disposed on a glove form on which it is made.

Referring now in detail to the Figures of the drawing, a seamless homogeneous integral film, glove 11 is formed on a glove form 21 which may be of standard configuration with fingers 23 and a frontal thumb 25 connecting with a palm zone 27. The form 21 may be of conventional material such as porcelain, and is provided with a textured surface 21a about its major hand engaging area, including the entire area over the fingers, thumb and hand body. If desired, the wrist zone 21b may be glazed to provide a smooth surfaced cuff surface which is generally considered to aid in rolled bead 11c formation.

The textured inner hand-engaging surface 11a of the glove 11 is transfer textured as a direct transfer function of the texture of the mold form in this zone. While any desired pattern or degree of texture roughness may be employed as desired for a given application, a preferred textured form surface 21a for surgical and medical examination gloves has been found to be provided by a sandblasted porcelain ceramic form 21 which has a surface finish 21a about the same as fine sandpaper. Transfer texturing or roughening from such a sandblasted surface 21a provides a highly desirable interior stippled hand-engaging surface.

The exterior textured surface 11b of the glove 11 is formed by impacting the gripping surfaces with fine droplets of an aqueous rubber latex solution, as more fully described hereinafter.

Figure 2:
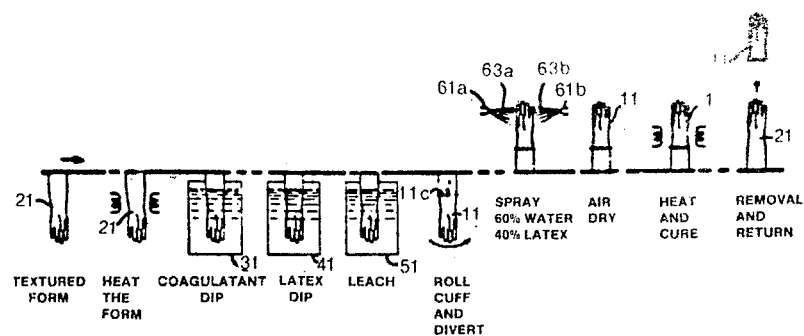
FIG. 2 illustrates schematically a flow sequence for manufacture of a glove according to the invention.

In the formation of a dual surface textured glove according to the method of my invention, each form or forms 21, which may be suitably mounted on a desired carrier, such as a movable board 29 or a conveyor chain, is carried sequentially through a series of steps as illustrated schematically in FIG. 2. Form 21 is dipped into a slip dip bath of conventional natural rubber latex in the normal manner to form a film on the form, as shown in the fourth segment of FIG. 2. In forming this film it is preferable to precede the rubber latex dip step by dipping the form 21 in a bath of suitable coagulant material, which may be of conventional composition, in order to increase the rate of latex film formation and decrease the time for such formation. As an aid to fast coagulant liquid evaporation the form 21 may be preheated before dipping into the coagulant, thereby quickly providing a desired positively charged form coagulant coating for coagulation of the negatively charged rubber latex onto the form during the latex dip operation. For surgical gloves the basic dried and cured film thickness may suitably be of the order of approximately 0.004–0.006 inch, with an impact crater build-up palm and finger gripping zone thickness (as later described) of approximately 0.005–0.008 inch, although increases or decreases in these dimensions may of course be made as may be desired for a particular use.

The latex dip may be of any desired rubber content, a conventional mix being approximately 40% solids and 60% water, with such heat curing and other agents therein as may be desired. Between each of the dip steps a short drying interval takes place, and if desired the forms may be angularly moved and/or rotated or otherwise moved to aid in evening the film formation on the forms 21.

After the aqueous rubber latex dip the glove film on the form 21 is subjected to a conventional leaching, as with water, to remove the coagulant, after which the cuff is conventionally rolled to form a bead 11c and is inverted for the next operation.

The glove film on the now inverted form is thereupon sprayed with an aqueous mix of uncured rubber latex, which is preferably of the same composition as the latex slip dip, and which may be adjusted to a desired viscosity, as by using more or less percentage of water, for spraying, to form a fine droplet spray. The spray droplets are impacted onto and form a homogeneous integral part of the uncured partially dried slip dip glove film. It is an important feature that the latex droplets are impacted onto the surface from two sources, angularly differently directed, and preferably intersecting spray relation, to afford effective coverage of the glove gripping surfaces including the palm, fingers, and thumb.

Figure 3:
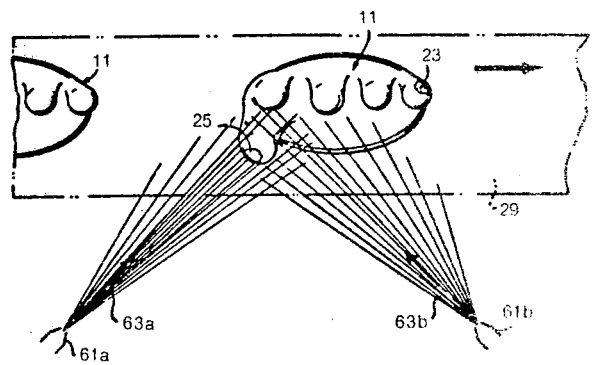
FIG. 3 is a plan view illustrating schematically the impact spraying of the dipped glove film.
Figure 4:
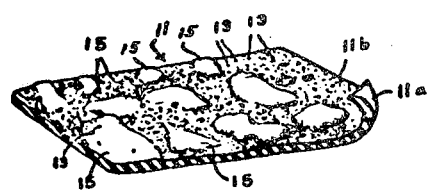
FIG. 4 is an enlarged (e.g. of the order of 10–20×) fragmentary schematic view of a typical section of the glove film in the double textured palm and finger gripping zones.

The presently preferred arrangement incorporates two conventional spray nozzles 61a, 61b, of the type employed to spray conventional paint mixes, the nozzles 61a, 61b being substantially horizontal and directed at approximately 45° to the palm face of the glove form 21 and to the longitudinal path of motion of the forms 21 past the nozzles. The center lines of the nozzle sprays (as indicated by the arrows in FIG. 3) are thus approximately normal to one another in this preferred arrangement and method, and the spray from the nozzles not only impacts from the two basic angularly opposed nozzle directions onto the glove film, but also impacts at different angles through the fanning out action of the individual sprays, and as the glove form passes longitudinally in front of the nozzles thereby aiding in affording wide impact droplet coverage of the various gripping surfaces of the glove. In addition, the spatial intersection of the paths of the droplets from the two spray sources in front of the glove form aids in providing coverage on the inner or crotch-facing surface of the thumb film which faces toward the palm of the form 21. This latter action will be appreciated as being generally enhanced by the intersection of the differently directed spray droplets in the zone between the thumb 25 and the palm 27 of the form 21 as the form passes the nozzles, which intersection of particles causes random vector scattering motion of the droplets, including collision-rebound droplet motion onto the thumb inner surface, in addition to such angular coverage of this and the other gripping surfaces as is afforded by the basic angular directions of the nozzles 61a, 61b toward the glove form. The glove forms 21 are traversed along a rectilinear path as illustrated, or alternatively such may be traversed along an arcuate path, past the nozzles and this may be effected in either lateral direction therepast. As will be apparent from FIGS. 2 and 3, and the foregoing description, the effect during such rectilinear movement of the form past the intersecting spray is to vary or change the effective zones of intersection and angles of intersection of the spray from the two sources over the frontal and side faces of the film on the form during and as a function of such rectilinear motion of the form toward, past and away from the spray zone, and as a function of the instant position of the glove form in relation to the spray paths of the two spray nozzles 61a, 61b, without requiring rotational or angular movement of either the form or the spray sources.

The center lines of the nozzles are preferably directed along lines intersecting the central sections of the fingers 23 and thumb 25, thereby affording good coverage of the palm, finger and thumb gripping areas. Droplet coverage of the wrist or cuff zone is of no functional value, and is optional. Thus, the spray nozzles may have their spray patterns relatively tight as may be desired, and the nozzles may be spaced relatively close, e.g. approximately a foot or less, to the glove film surface so as to conserve materials, if desired.

Figure 5:
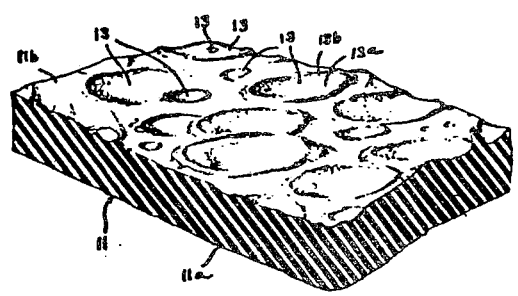
FIG. 5 is a further enlarged (e.g. of the order of 100–200×) fragmentary schematic view of a section of the double textured glove film schematically illustrating an impact crater zone.

The fine droplets of the latex spray impact onto the uncured latex film surface and form tiny craters, which appear to be similar to those formed by meteoritic impact with the earth or moon, the craters generally having a central dish-shaped central zone surrounded by a raised rim zone which protrudes above the surrounding impacted area. The droplets thus serve to build up the film surface and to form dish-shaped depressions and protruding cup shaped rims. These droplet impact craters are highly multiplied in nature and, as with other randomly impacted surfaces, the craters will overlap, as shown schematically in the enlarged schematic Figures of the drawing (see particularly FIG. 5). As will be appreciated, the size, quantity, and density of the impact craters will vary widely, and the drawings are schematic and illustrative only, not necessarily being to scale or illustrating any specific actual impact build-up zone.

The particular extent of build-up impacted spray droplet craters on the glove film may be adjusted as desired by varying the spray pressure and viscosity and the rate of feed of the glove forms 11 past the nozzles 61a, 61b. A preferred degree of build-up of the droplet impact cratered surface has been found to exist when the droplets begin to accumulate in random areas to form fluid plateau-like mesa areas 15, thereby providing a composite surface of impact droplet craters 13 and free-form plateau-like raised mesa zones 15 randomly interspersed on the film surface 11b. The mesa zones in various instances also appear to have some small randomly spaced impact craters, depressions or ridges formed on their surface, although such are not as prominent as in the interspace zones between mesas and the mesa surfaces appear to be generally more flat than the zones therebetween and which may be effectively substantially covered with spaced and overlapping impact craters.

The precise nature of the formation of this desirable impact crater textured surface is not fully understood; however, as the tiny droplets have a high content of water it is speculated that the crater control zone dish depressions tend to become more exaggerated upon drying of the water from the craters, and the mesa zones appear to be an accumulation of impact droplets which form small raised liquid "lakes" held in place by their own liquid surface tension and which dry generally smoother than the lesser accumulative or non-accumulative impact droplet crater areas therebetween.

As stated above, this is the preferred impact latex droplet textured surface, although more or less extent of impacting, and consequent increase or decrease in impact overlap and accumulation, may be employed if desired.

After latex spraying, the glove film 11 is air dried and then cured as by heating in a conventional manner, and may then be removed from the form 21, after which the form may be recycled.

The net result is a seamless homogeneous rubber latex glove which is soft, and pliable, affords excellent sensitivity for surgical and medical purposes, and has highly desirable textured surfaces on both its inner and outer surfaces, thereby providing for ease of donning, minimizing causation of dermatitis, anti-skid action on a perspiring hand during surgery, and enhanced friction gripping particularly by the multiple suction cup-like impact craters and ridged surfaces of the exterior surface.

While the invention has been shown and described with respect to a particular illustrative embodiment, it will be apparent to those skilled in the art that various modifications and improvements may be made without departing from the scope and spirit of the invention. Accordingly, the invention is not to be restricted by the particular illustrative embodiment, but only by the scope of the appended claims.

That which is claimed is:

1. The method of forming a roughened surface glove comprising dip-forming and partially air-drying a coating of aqueous solution of rubber latex while in contiguous film-covering relation on a desired use portion of a hand-shaped glove form having fingers and a thumb, to form an uncured film of rubber latex on said form with an inner surface having a mirror image of the film-covered portion of the outer surface of the form, externally spraying an aqueous liquid latex solution in droplet form onto the outer surface of said film in the palm, finger and thumb-gripping zones formed thereby, and while said film is in an uncured condition, to thereby form a rough external surface on said film, and curing and removing the resulting latex-droplet-impacted glove film including the impacted latex droplet solution thereon, from said form, said external spraying being effected by simultaneously directing a spray of said liquid latex soltuion from two sources and in two intersecting path directions of latex spray toward the palm side of said form while effecting relative motion between said form and said spray sources to effect relative effective rectilinear movement of said form along a path extending toward, in front of and laterally past and away from said two spray sources of liquid latex solution while thereby varying the effective zones of intersection and angles of intersection of the spray from said two sources with said uncured film as a function of said rectilinear motion of said form toward, past and away from said spray.

2. The method according to claim 1, said relative motion being a single pass rectilinear relative motion between said form and said spray sources.

3. The method according to claim 2, further comprising:

forming said dip-formed coating film on said glove form by dipping said form into a coagulant bath, and then dipping said form into a bath of liquid rubber latex to cover the desired area of said glove form.

4. The method according to claim 2, said relative movement being effected by rectilinear advancement of said glove form along a rectilinear path extending relatively toward, through, and away from, a general intersection zone of the spray from said two sources, while maintaining said glove form with its palm and thumb side facing generally toward said spray sources.

5. The method according to claim 1, including melding the droplets as an integral part of said film upon impact with the surface of said film to an extent to form droplet interconnections and random mesa build-ups, and subsequently generally randomly impacting subsequent droplets smaller than said mesa build-ups onto said mesa build-ups to form randomly cratered integral film mesas on the surface of said film.

6. The method according to claim 1, said spray being directed toward the palm side of said glove form, the thumb portion of said form being disposed on the palm side of said form and having a thumb crotch zone generally rearwardly of the thumb intersection with the palm zone thereof, and directing the paths of spray from said two sources at intersecting angles such that the droplets from the respective two sources intersect in a zone surrounding and rearward of said thumb and thereby aid in spray coating the crotch and rear surface of the film formed on said thumb.

7. The method according to claim 1, the fingers on said glove form each having a central section, said spraying being a fan-shaped spray and the center line of each of said directions of spraying being directed toward said central sections of the fingers on said glove form.

8. The method according to claim 7, said spray center lines intersecting at an angle to one another substantially less than 180° and each extending toward and at an acute angle to a plane extending generally through the palm and fingers of said form and along the line of direction of motion of said form along said path.

9. The method according to claim 7, wherein said spray center lines intersect in front of the palm face of said glove form.

10. The method according to claim 7, wherein said glove form has a crotch-facing surface, and where said portions of said spray intersect rearwardly of the thumb crotch-facing surface of said glove form.

11. The method according to claim 1, wherein said dip-forming and partial air-drying of a quantity of an aqueous solution of rubber latex is effected on a glove form having a roughened outer surface, to form a film of rubber latex on the form with an inner surface roughened as a mirrored image of the film-covered portion of the corresponding roughened outer surface of the form, and thereby forming a double-roughened surface glove, one of which roughened surfaces is a mold-image mirror replica and the other of which surfaces is a composite of impact-bombardment accumulations and craters.

12. A method of forming a glove provided with a roughened surface area which comprises:

dip-forming and partially air-drying a layer of an aqueous solution of rubber latex on the surface of a hand-shaped glove form having palm, thumb and fingers forming surfaces, to form an uncured latex film thereon, externally spraying an aqueous liquid latex solution in minute droplet form along two intersecting latex spray pattern paths from two simultaneous effectively different source zones from which the respective general spray pattern paths of latex spray droplets are simultaneously angularly differently directed relative to one another onto the outer surface of said film in the palm, finger and thumb-gripping zones formed thereby, by impacting such outer surfaces with the spray droplets to form impact craters in said film while said film is in an uncured condition on its air-exposed surface to thereby form a roughened impact cratered surface on said film, discontinuing said spraying when the desired impact-roughened areas are produced, and curing the resulting latex-droplet-impacted glove film, including the impacted latex droplet solution thereon, on said form, and removing the cured film from said form.

13. The method according to claim 12, further comprising:

forming said film on said glove form by dipping said form into a coagulant bath and then dipping said form into a bath of liquid rubber latex to cover the desired area of said glove form.

14. The method according to claim 12, further comprising:

forming a roughened surface on the surface of said glove film contiguous with said form by forming said film on a form having a roughened surface area on which at least a portion of said film is formed.

15. The method according to claim 12, further comprising:

including melding impact droplets as an integral part of said film upon impact with the surface of said film, then drying and heat-curing and removing the spray droplet impacted film from said form.

16. The method according to claim 12, said external spraying being effected by directing spray from two sources and in two nonparallel directions toward the palm side of said form.

17. The method according to claim 12, in which said two angularly differently directed source zones have spray patterns which intersect one another.

18. The method according to claim 17, including effecting relative rectilinear motion between said glove form and said spray source zones to effect the movement of said glove form relatively toward, through and away from the general intersection reaction zone of the spray from said two spray source zones, while maintaining said glove form with its palm and thumb side facing generally toward said spray source zones.

19. The method according to claim 17, said spray being directed toward the palm side of said glove form, the thumb portion of said form being disposed on the palm side of said form and having its crotch zone generally rearwardly of the thumb intersection with the palm zone thereof, and directing the paths of spray from said two spray source zones at intersecting angles such that droplets from the respective two spray source zones intersect in the zone surrounding and rearward of said thumb and thereby aid in spray-coating the crotch and rear surface of the film formed on said thumb.

20. The method according to claim 17, said spraying being a fan-shaped spray and the center line of each of said directions of spraying being directed toward a central zone of the respective fingers on said glove form.

21. The method according to claim 20, said glove form being held upright and said spray center lines being substantially horizontal and intersecting at approximately right angles to one another.

22. The method according to claim 21, wherein said spray center lines intersect in front of the palm face of said glove form.

23. The method according to claim 21, wherein portions of said spray intersect rearwardly of the thumb crotch-facing surface of said glove form.

24. The method according to claim 12, including randomly melding various droplets as an integral part of said film upon impact with the surface of said film to an extent to form droplet interconnections and random mesa build-ups and subsequently generally randomly impacting subsequent droplets smaller than said mesa build-ups onto said mesa build-ups to form randomly cratered integral film mesas on the surface of said film.

* * * * *

UNITED STATES PATENT AND TRADEMARK OFFICE
CERTIFICATE OF CORRECTION

PATENT NO. : 4,329,312

DATED : May 11, 1982

INVENTOR(S) : Rudolph V. Ganz

It is certified that error appears in the above-identified patent and that said Letters Patent are hereby corrected as shown below:

Column 4, Line 58, change "control" to ---central--- .

Column 5, Lines 44 and 45, change "soltuion" to ---solution--- .

Signed and Sealed this

Twenth-eighth Day of September 1982

[SEAL]

Attest:

Attesting Officer

GERALD J. MOSSINGHOFF

Commissioner of Patents and Trademarks